United States Patent [19]

Sullivan

[11] 4,362,742
[45] * Dec. 7, 1982

[54] METHOD FOR TREATING SKIN DISORDERS

[76] Inventor: Thomas J. Sullivan, 25 Old Gate Rd., Thrussington, Leicestershire, England

[*] Notice: The portion of the term of this patent subsequent to Jun. 2, 1998, has been disclaimed.

[21] Appl. No.: 251,177

[22] Filed: Apr. 6, 1981

Related U.S. Application Data

[63] Continuation of Ser. No. 530,853, Dec. 9, 1974, Pat. No. 4,271,182.

[30] Foreign Application Priority Data

Dec. 19, 1973 [GB] United Kingdom ............... 58986/73

[51] Int. Cl.$^3$ ............................................. A61K 31/35
[52] U.S. Cl. .................................................. 424/283
[58] Field of Search ........................................ 424/283

[56] References Cited

U.S. PATENT DOCUMENTS 3,686,412  8/1972  Fitzmaurice et al. ................ 424/283
4,271,182  6/1981  Sullivan ................................ 424/283

OTHER PUBLICATIONS

Berrens, Chemical Abstracts 74:138544q, (1971).
Merck Manual, 12th Ed., pp. 1458-1463, (1972).
Easty et al., Clinical Allergy, vol. 2, pp. 99-107, (1972).
Stedman's Medical Dictionary, pp. 502, 160-161 & 427-428, (1966).
Physicians Desk Reference, pp. 836 & 1170-1171, (1971).

*Primary Examiner*—Leonard Schenkman
*Attorney, Agent, or Firm*—Merriam, Marshall & Bicknell

[57] ABSTRACT

The present invention relates to methods of treating chronic skin disorders by externally applying to the skin compounds by the following formula

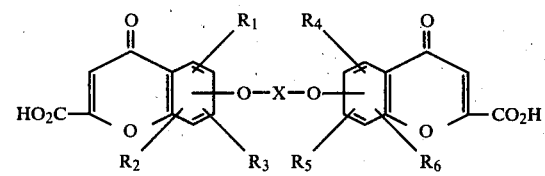

and therapeutically acceptable salts, esters and amides thereof, wherein $R_1$ through $R_6$ and X are as hereinafter defined.

1 Claim, No Drawings

METHOD FOR TREATING SKIN DISORDERS

This is a continuation of application Ser. No. 530,853, filed Dec. 9, 1974, now U.S. Pat. No. 4,271,182.

The present invention relates to a new method for treating diseases of the skin.

Compounds of the general formula

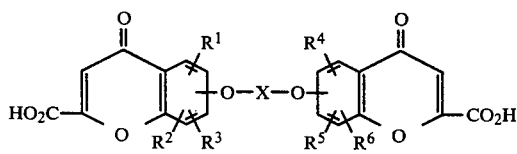

and therapeutically acceptable salts, esters and amides thereof, [wherein $R^1$, $R^2$, $R^3$, $R^4$, $R^5$ and $R^6$ are the same or different and each is H or halogen, lower alkyl, hydroxy, lower alkoxy, lower alkenyl, benzyloxy, nitro, substituted lower alkyl or substituted lower alkoxy, and X is a saturated or unsaturated, substituted or unsubstituted, straight or branched polymethylene chain which may be interrupted by one or more carbocyclic rings or oxygen-containing heterocyclic rings, oxygen atoms or carbonyl groups,] have been proposed for use in the treatment of the allergic disorders, notably allergic asthma, by administration by inhalation of a powder formulation or of a nebulised aqueous formulation.

Surprisingly, we have not found that these compounds have pharmacological activity when administered externally to the skin of a mammal and are thus indicated for use in the treatment of chronic skin disorders in mammals, e.g. man.

Accordingly, the present invention provides a method for the treatment of chronic skin disorders which comprises the external application of an effective amount of a compound of general formula I or a pharmaceutically acceptable salt, ester or amide thereof to the skin of a mammal suffering from a chronic skin disorder.

We prefer to use those compounds of formula I in which $R^1$, $R^2$, $R^3$, $R^4$, $R^5$ and $R^6$ are the same or different and each is a hydrogen or halogen atom (e.g. a chlorine, bromine, iodine or fluorine atom), a lower alkyl (e.g. a methyl, ethyl, propyl, isopropyl, butyl or tertiaryl butyl group), hydroxy, lower alkoxy (e.g. a methoxy, ethoxy, propoxy, isopropoxy, butoxy or tertiary butoxy group) or substituted lower alkyl or lower alkoxy group, (for example a hydroxyloweralkoxy, loweralkoxyloweralkoxy, carboxyloweralkoxy, hydroxyloweralkyl or haloloweralkyl such as chloro-, bromo, iodo- or fluoro-loweralkyl, a loweralkenyl, e.g. allyl or methyl-allyl, benzyl or nitro, and X is a saturated or unsaturated, substituted or unsubstituted, straight or branched polymethylene chain which may be interrupted by one or more carbocyclic rings or oxygen containing heterocyclic rings, (e.g. benzene, dioxan, tetrahydrofuran, or dihydropyran rings), oxygen atoms or carbonyl groups.

In general, it is preferred that no more than one of $R^1$, $R^2$ and $R^3$ and no more than one of $R^4$, $R^5$ and $R^6$ is other than hydrogen and are selected from a hydrogen or halogen atom or an alkyl, hydroxy, alkoxy or substituted alkoxy group, and X has the meaning defined above.

Particularly preferred compounds of formula I are those in which all of $R^1$, $R^2$, $R^3$, $R^4$, $R^5$ and $R^6$ are hydrogen.

The group X may be any of a wide variety of groups. Thus, for example, it may be a straight or branched saturated or unsaturated hydrocarbon chain. Further, X may be such a chain interrupted by one or more oxygen atoms, carbonyl groups or carbocyclic or heterocyclic rings and may be substituted by one or more halogen atoms (e.g. chlorine, bromine, iodine or fluorine atoms), or hydroxy or lower alkoxy (e.g. methoxy, ethoxy, propoxy, isopropoxy, butoxy, tert- butoxy, etc) groups. Specific examples of the group X are groups of the formulae:

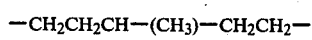

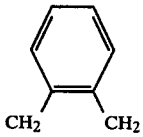

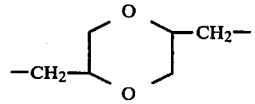

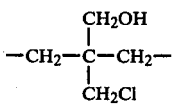

etc. The group X is preferably a straight or branched hydrocarbon chain, which may be interrupted by one or more oxygen atoms, and contains from 3 to 7 carbon atoms. Desirably such a chain is a polymethylene chain substituted by one or more hydroxyl groups, a particularly preferred chain being the 2-hydroxy-trimethylene chain ($-CH_2CHOHCH_2-$).

The chain $-O-X-O-$ may link different or corresponding positions on the chromone molecules.

Thus, the preferred compounds of formula I for present use are those of the general formula:

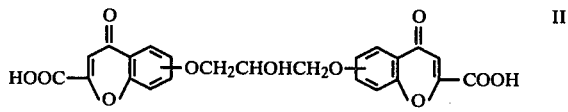

Suitable pharmaceutically acceptable salts include, for example, ammonium salts, alkali-metal salts (e.g. sodium, potassium and lithium), alkaline-earth metal salts (e.g. magnesium and calcium), and salts with organic amines (e.g. mono-, di- or tri- alkyl $C_{1-6}$ amines, piperidine, and trialkanol $C_{1-6}$ amine salts). Esters which may be mentioned include simple alkyl esters (e.g. methyl, ethyl, propyl, isopropyl, butyl and tertiary butyl esters). Amides which may be mentioned include simple amides (for example amides with ammonia and lower alkylamines such as methylamine, ethylamine etc.) and more complex amides with amino acids, e.g. glycine.

Specific compounds of formula I and derivatives thereof for present use are:

Disodium salt of 1,3-bis(2-carboxychromon-5-yloxy)-propane.
Disodium salt of 1,3-bis(2-carboxychromon-5-yloxy)-2-hydroxypropane.
1,3-Bis(2-carboxychromon-5-yloxy)-2-hydroxypropane.
Calcium salt of 1,3-bis(2-carboxychromon-5-yloxy)-2-hydroxypropane.
Magnesium salt of 1,3-bis(2-carboxychromon-5-yloxy)-2-hydroxypropane.
Dipiperidine salt of 1,3-bis(2-carboxychromon-5-yloxy)-2-hydroxypropane.
1,12-Bis(2-carboxychromon-5-yloxy)-2,11-dihydroxy-4,9-dioxadodecane.
1,4-Bis(2-carboxychromon-5-yloxy)butane.
1,5-Bis(2-carboxychromon-5-yloxy)pentane.
1,6-Bis(2-carboxychromon-5-yloxy)hexane.
1,10-Bis(2-carboxychromon-5-yloxy)decane.
1,7-Bis(2-carboxychromon-5-yloxy)-2,6-dihydroxy-4-oxaheptane.
1,5-Bis(2-carboxychromon-5-yloxy)-3-oxapentane.
1,4-Bis(2-carboxychromon-5-yloxy)-2,3-dihydroxybutane.
1,4-Bis(2-carboxychromon-5-yloxy)-2-hydroxybutane.
1,5-Bis(2-carboxychromon-7-yloxy)pentane.
1,10-Bis(2-carboxychromon-5-yloxy)-3,8-dioxa-4,7-dioxodecane.
1,5-Bis(2-carboxy-8-chlorochromon-5-yloxy)pentane.
1-(2-Carboxychromon-5-yloxy)-3-(2-carboxychromon-7-yloxy)-2-hydroxypropane.
1-(2-Carboxychromon-5-yloxy)-5-(2-carboxychromon-7-yloxy)pentane.
1,3-Bis(2-carboxy-7-methylchromon-5-yloxy)-2-hydroxypropane.
1,3-Bis(2-carboxy-8-ethylchromon-5-yloxy)-2-hydroxypropane.
1-(2-Carboxychromon-5-yloxy)-3-(2-carboxy-8-ethylchromon-5-yloxy)-2-hydroxypropane.
1,5-Bis(2-carboxychromon-8-yloxy)pentane.
1,5-Bis(2-carboxy-8-methylchromon-7-yloxy)pentane.
1,3-Bis(2-carboxy-8-methylchromon-7-yloxy)-2-hydroxypropane.
1,5-Bis(2-carboxychromon-5-yloxy)-3-methylpentane.
1,3-Bis(2-carboxy-6-chlorochromon-7-yloxy)-2-hydroxypropane; disodium salt.
1-(2-Carboxychromon-5-yloxy)-3-(2-carboxy-6-chlorochromon-7-yloxy)-2-hydroxypropane; disodium salt.
1,5-Bis(2-carboxychromon-6-yloxy)pentane.
1,3-Bis(2-carboxychromon-7-yloxy)-2-hydroxypropane.
1,2-Bis(2-carboxychromon-5-yloxymethyl)benzene.
1,3-Bis(2-carboxychromon-6-yloxy)-2-hydroxypropane.
Disodium salt of 1-(2-carboxychromon-5-yloxy)-3-(2-Carboxychromon-6-yloxy)-2-hydroxypropane.
Disodium salt of 1-(2-carboxychromon-5-yloxy)-3-(2-Carboxychromon-8-yloxy)-2-hydroxypropane.
1,8-Bis(2-carboxychromon-5-yloxy)octane.
1,9-Bis(2-carboxychromon-5-yloxy)nonane.
1,2-Bis(2-carboxychromon-5-yloxy)ethane.
1,3-Bis(2-carboxychromon-5-yloxy)-2-chloromethyl-2-hydroxymethylpropane; dipotassium salt tetrahydrate.
Disodium salt of 1,3-bis(2-carboxychromon-5-yloxy)-2-ethoxypropane.
Disodium salt of 1,3-bis(2-carboxychromon-5-yloxy)-2-oxopropane.
Diethyl ester of 2,5-bis(2-carboxychromon-5-yloxymethyl)-dioxan.
11,3-Bis(2-carboxy-7-methoxychromon-5-yloxy)-propan-2-ol.
1,5-Bis(2-carboxy-7-methoxychromon-5-yloxy)-pentane.
1,3-Bis(2-carboxy-5(2-hydroxypropoxy)chromon-7-yloxy)propan-2-ol.
1,3-Bis(2-carboxy-7-(2-hydroxypropoxy)chromon-5-yloxy)-propan-2-ol.
1,5-Bis(2-carboxy-5-methoxychromon-7-yloxy)-pentane.
1,5-Bis(2-carboxy-7-(2-hydroxypropoxy)-chromon-6-yloxy)-pentane.
1,3-Bis(5-benzyloxy-2-carboxychromon-7-yloxy)-propan-2-ol.
1,3-Bis(2-carboxy-5-methoxy-chromon-7-yloxy)-propan-2-ol.
1,3-Bis(2-carboxy-5-hydroxychromon-7-yloxy)-propan-2-ol.
1,3-Bis(8-allyl-2-carboxychromon-5-yloxy)-propan-2-ol.
1,3-Bis(8-allyl-2-carboxychromon-7-yloxy)-propan-2-ol.
1-(8-Allyl-2-carboxychromon-7-yloxy)-3-(2-carboxychromon-7-yloxy)-propan-2-ol.
1,3-Bis(2-carboxy-8-methallylchromon-7-yloxy)-propan-2-ol.
1,3-Bis(8-allyl-6-bromo-2-carboxychromon-7-yloxy)-propan-2-ol.
1-(8-Allyl-2-carboxychromon-7-yloxy)-3-(2-carboxychromon-6-yloxy)-propan-2-ol.
1,5-Bis(8-allyl-2-carboxychromon-7-yloxy)-pentane.
1,3-Bis(2-carboxy-8-nitrochromon-5-yloxy)-propan-2-ol.

The compound of formula I or a pharmaceutically acceptable salt, ester or amide thereof may be applied to the skin of the mammal, notably man, in any suitable formulation. Thus, the compound of formula I may be formulated as an ointment, in which the finely ground compound of formula I is dispersed in a soft paraffin. Liquid paraffin, hard paraffin, and wool fat may be included in the ointment base. If a water miscible ointment base is desired, a polyethylene glycol may be included.

The compound of formula I may also be formulated as a cream, which may be either an oil in water type, or a water in oil type. Suitable emulsifying agents for the former type include sodium, potassium, ammonium and triethanolamine soaps; polysorbates; and cationic, anionic, and non-ionic emulsifying waxes. Suitable emulsifying agents for the latter type include calcium soaps, wool fat, wool alcohols, beeswax, and certain sorbitan esters. A preservative is usually desirable in a cream, particularly in an aqueous cream. Examples of suitable preservatives alone, or in combination, are chlorocresol, p-hydroxybenzoates, thiomersal, and chlorbutol.

The compound of formula I may also be formulated as a lotion or liniment by dissolving or dispersing the compound in an aqueous or oily base. A suitable preservative may be included in the formulation. Ethanol and/or glycerin may be included in the aqueous base. Examples of suitable oil bases include arachis oil, castor oil, and other vegetable oils. Where pastes or gels are desired, a thickening agent may be incorporated in an aqueous base. These ingredients may also serve as stabilising agents for emulsions. Suitable agents include Carbopol, bentonite, soluble cellulose derivatives (e.g. sodium carboxy methyl cellulose, hydroxypropyl methyl cellulose), Veegum and polyvinyl alcohol.

Other ingredients e.g. humectants, antioxidants, perfumes and pigments may also be present if desired.

The compound of formula I may also be formulated as a dusting-powder, in which two or more ingredients are intimately mixed in fine powder form. Alternatively, the compound of formula I may be applied as a solution or suspension in a liquid carrier to the surface of a solid carrier and the coated particles dried. Examples of solid carriers, which are normally sterilised, are talc, starch, lactose, zinc oxide, light kaolin, calcium carbonate.

A semi-solid base that has been found particularly suitable is based on a fatty alcohol/glycol mixture. Suitable fatty alcohols include saturated alkanols containing 16 to 24 carbon atoms and suitable glycols include 1,2-propylene glycol, 1,3-propylene glycol, polyethylene glycols of molecular weight 100 to 800, and dipropylene glycol. The fatty alcohol and glycol are present in from 15 to 45:45 to 85 parts by weight, preferably 20 to 35:55 to 80 parts, respectively. If desired a plasticizer, e.g. a polyethylene glycol of molecular weight 800 to 20,000 or 1,2,6-hexanetriol, and/or a penetrant may also be present.

Typical formulations of the compound of formula I are illustrated by the following Examples:

| 1. | Ointment | |
|---|---|---|
| | Compound of formula I | 10% w/v |
| | Liquid paraffin BP | 10% w/v |
| | Wool Fat BP | 10% w/v |
| | White Soft Paraffin BP | 70% w/v |
| 2. | Water Miscible Ointment | |
| | Compound of formula I | 10% w/v |
| | Polyethylene glycol 400 | 40% w/v |
| | Polyethylene glycol 4000 | 50% w/v |
| 3. | Aqueous Cream | |
| | Compound of formula I | 10% w/v |
| | Emulsifying Ointment BP | 30% w/v |
| | Chlorocresol | 1% w/v |
| | Purified Water | 59% w/v |
| 4. | Oily Cream | |
| | Compound of formula I | 10% w/v |
| | Wool alcohols BP | 3% w/v |
| | Hard paraffin BP | 12% w/v |
| | White Soft Paraffin BP | 10% w/v |
| | Liquid Paraffin BP | 30% w/v |
| | Purified Water | 35% w/v |
| 5. | Lotion (Aqueous) | |
| | Compound of formula I | 10% w/v |
| | Glycerol | 20% w/v |
| | Alcohol (95%) | 20% w/v |
| | Sodium Carboxymethyl Cellulose | 1% w/v |
| | Purified Water | 49% w/v |
| 6. | Lotion (Oily) | |
| | Compound of formula I | 10% w/v |
| | Arachis Oil | 90% w/v |
| 7. | Dusting Powder | |
| | Compound of formula I | 10% w/v |
| | Zinc Oxide | 25% w/v |
| | Purified Talc | 10% w/v |
| | Sterilisable Maize Starch | 55% w/v |

| | -continued | |
|---|---|---|
| 8. | Fatty alcohol/glycol base | |
| | Compound of formula I | 10% w/v |
| | Stearyl alcohol | 27% w/v |
| | Propylene Glycol | 63% w/v |

The compound of formula I is typically present in the above formulations in from 5 to 20% by weight, notably 10 to 15%. Where solid particles of the compound are present, e.g. in a suspension or dispersion or in a powder formulation, it is preferred that these have a predominant size of less than 10 micrometers.

The compositions for present use may be made using any appropriate technique, e.g. by dry mixing the solid ingredients or by grinding the solid ingredients together, or by emulsifying an aqueous solution of the compound of formula I with an appropriate oil base.

The compound of formula I or the derivative thereof is preferably administered to the patient merely by smearing a cream or paste over the affected area of the skin. Alternatively, the compound may be impregnated into a gauze or similar pad and this pad then applied to the affected area; or a powder containing the active ingredient may be puffed or dusted on to the affected area.

The rate of application of the compound of formula I will depend upon the severity and the surface area of the disorder to be treated and repeated applications may be made at intervals during the day, e.g. from 1 to 6 times a day.

The compounds of formula I or the pharmaceutically acceptable derivatives thereof find use in the treatment of chronic dermatoses in mammals, notably man. Dermatoses which may be treated include those involving skin mast cells and/or antibody/antigen reactions and include eczemas, drug eruptions, psoriasis, dermatitis herpetiformis, pemphigus and chronic skin ulcers, notably those affecting man in tropical climates. The compounds of formula I or derivatives thereof are of particular use in the treatment of atopic eczema in man.

EXAMPLE 9

Ointment formulations were prepared by mixing the disodium salt of 1,3-bis(2-carboxychromon-5-yloxy)2-hydroxypropane with a vaseline base to give ointments containing 5 or 10% by weight of the disodium salt. These ointments were applied to patients suffering from eczemas, notably atopic eczema, by smearing the ointments on to the affected areas of the skin from 2 to 4 times a day.

In 16 patients treated an improvement in pruritus was noted after 7 to 10 days and over the test period of 4 months the ointments continued to improve the skin. In some cases the improvement was at least as good as that which would have been expected with a steroid ointment.

From another aspect, therefore, the invention also provides a composition for topical application to the skin of a mammal notably man, which comprises a compound of formula I or a pharmaceutically acceptable salt, ester or amide, notably a compound of formula II or the disodium salt thereof; in admixture with a diluent suitable for topical application to the skin.

The term 'lower' is used herein in respect of values for $R^1$ to $R^6$ to denote that that group contains from 1 to 6 carbon atoms.

The compounds of formula I and their preparation are described in British Pat. No. 1144905.

I claim:

1. A method for treating drug eruptions, psoriasis, dermatitis herpetiformis, pemphigus or chronic skin ulcers in man which comprises externally applying a therapeutically effective amount of the compound, 1,3-bis(2-carboxychromon-5-yloxy)-2-hydroxypropane or a pharmaceutically acceptable salt, ester or amide thereof to afflicted areas of the skin.

* * * * *